United States Patent [19]

Bhiwandiwala et al.

[11] Patent Number: 4,467,806
[45] Date of Patent: Aug. 28, 1984

[54] OSMOTIC CERVICAL DILATOR

[75] Inventors: Pouru Bhiwandiwala, Chapel Hill; Robert G. Wheeler, Durham, both of N.C.

[73] Assignee: Repromed, Inc., San Antonio, Tex.

[21] Appl. No.: 472,385

[22] Filed: Mar. 10, 1983

Related U.S. Application Data

[63] Continuation of Ser. No. 257,816, Apr. 27, 1981, abandoned.

[51] Int. Cl.$^3$ .............................................. A61M 29/00
[52] U.S. Cl. .................................................. 128/341
[58] Field of Search ................. 128/130–132, 128/341; 604/890–897

[56] References Cited

U.S. PATENT DOCUMENTS

| | | | |
|---|---|---|---|
| 2,134,930 | 11/1938 | Reynolds | 128/285 |
| 3,867,329 | 2/1975 | Halpern et al. | 128/347 X |
| 3,961,629 | 6/1976 | Richter et al. | 128/296 |
| 4,077,408 | 3/1978 | Murray et al. | 128/285 |
| 4,090,013 | 5/1978 | Ganslaw et al. | 128/284 X |
| 4,237,893 | 12/1980 | Michaels | 128/341 |

OTHER PUBLICATIONS

Properties and Safety of Cervical Dilator, Amer. J. of Obstetrics & Gynecology, Wheeler et al., vol. 146, No. 6, pp. 597–601.

Primary Examiner—Teddy S. Gron
Assistant Examiner—T. J. Wallen
Attorney, Agent, or Firm—B. B. Olive

[57] ABSTRACT

An osmotic cervical dilator has a sponge-like synthetic plastic body in which all the residual void spaces in the body are filled with a salt composition and the body shaped for insertion and retention in the cervix of the patient. The dilator, once inserted and retained by the cervix, is adapted to draw and to expand by osmotic effect and to retain cervical fluids and particularly water contained in the cervix.

21 Claims, 4 Drawing Figures

OSMOTIC CERVICAL DILATOR

This application is a continuation of application Ser. No. 257,816 filed Apr. 27, 1981, now abandoned.

BACKGROUND OF THE INVENTION

1. Field of the Invention

This invention relates to devices for dilation of the cervix and particularly to such devices for dilation which do not require surgical procedures.

2. Description of the Prior Art

Dilation of the cervix is an extremely common gynecological procedure which is performed for several diagnostic and therapeutic indications. The cervix can be dilated rapidly, in seconds or a few minutes, or gradually over a period of hours, up to 24 hours. Rapid dilation is a surgical procedure and metal or plastic dilator rods of increasing diameter are used to dilate the cervix. This procedure is painful and requires local or general anesthesia. The metal dilators can cause trauma to the cervix resulting in short and long-term adverse side-effects.

Slow dilation can be performed by introducing laminaria tents, made of seaweed, into the cervical canal. These tents gradually swell up resulting in an adequate dilation of the cervix in approximately 24 hours. The introduction of the tent only causes minimal discomfort to the patient and, therefore, does not require local or general anesthesia. Conventional laminaria dilators are furnished in various diameters for the physician to select based on the size of the internal os of the cervix and on the desired final diameter of dilation. Since the process of dilation is so gradual, the possibility of traumatizing the cervix is minimal and there are no associated long-term side-effects. However, the laminaria tents now available are very expensive and are not easily available in the developing countries.

Therefore, the object of the present invention is to provide a tent-type osmotic cervical dilator which is inexpensive to manufacture and which would, therefore, be available to the developing countries at minimal cost.

SUMMARY OF THE INVENTION

A tent-type osmotic cervical dilator comprises a polyvinyl alcohol foam body of at least 80% porosity and having a magnesium sulfate composition loaded into the body and the body compressed and shaped into a rod for insertion and retention in the cervix of the patient.

DESCRIPTION OF THE PREFERRED EMBODIMENT

Figure 1:
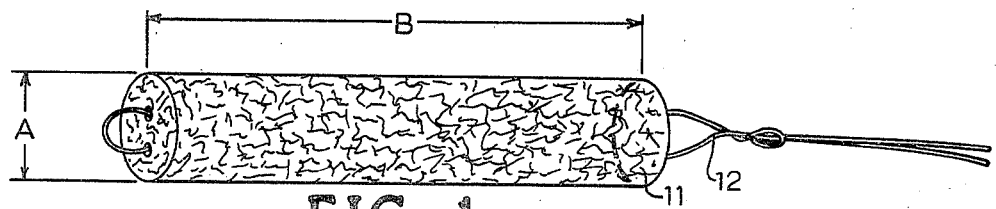
FIG. 1 is a perspective view of an osmotic cervical dilator according to the present invention prior to being compressed.
Figure 4:
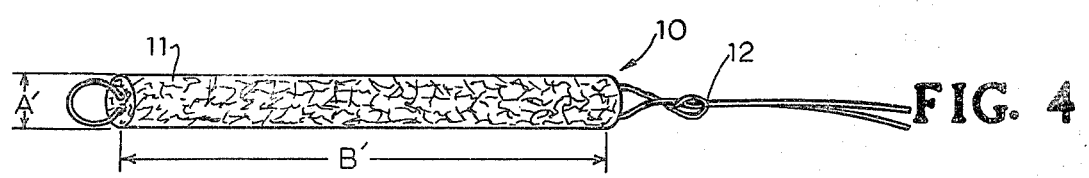
FIG. 4 is a perspective view of the dilator after being compressed into a rod shape ready for insertion.

Turning now to a description of the drawings, osmotic cervical dilator 10 of the present invention is illustrated in FIG. 4. A description of how osmotic cervical dilator 10 is made will aid in clarification of how it operates and how it represents a unique method of cervical dilation. A cylindrical sponge 11, as illustrated in FIG. 1, with a diameter A of 8 to 20 mm and a length B of 50 to 80 mm is fitted with a string 12 running from one end to the other and returned as illustrated in FIG. 1. The purpose of string 12 is to facilitate removal of dilator 10 from the cervix and to insure sponge 11 will not be pulled into two parts.

Next, sponge 11 is placed in a saturated solution of a tissue compatible salt of high osmotic activity preferably magnesium sulfate and the voids in sponge 11 are filled by vacuum impregnation, boiling or prolonged submersion. Polyvinyl alcohol, polyurethane, silicone, collagen or other biocompatible material in the form of a sponge with connecting porosity may be used for cylindrical sponge 11. Filled sponge 11 is then removed from the solution and allowed to dry until it weighs about 105% of its weight when it is completely dry.

Figure 2:
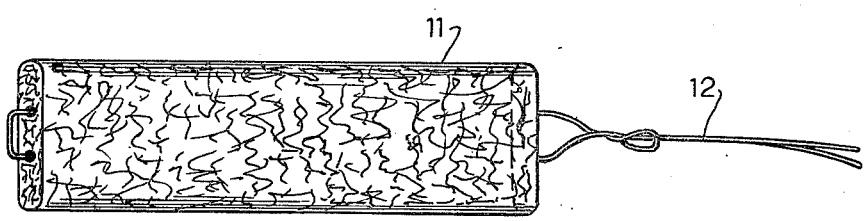
FIG. 2 is a perspective view of the foam material of FIG. 1 compressed into a slab shape.
Figure 3:
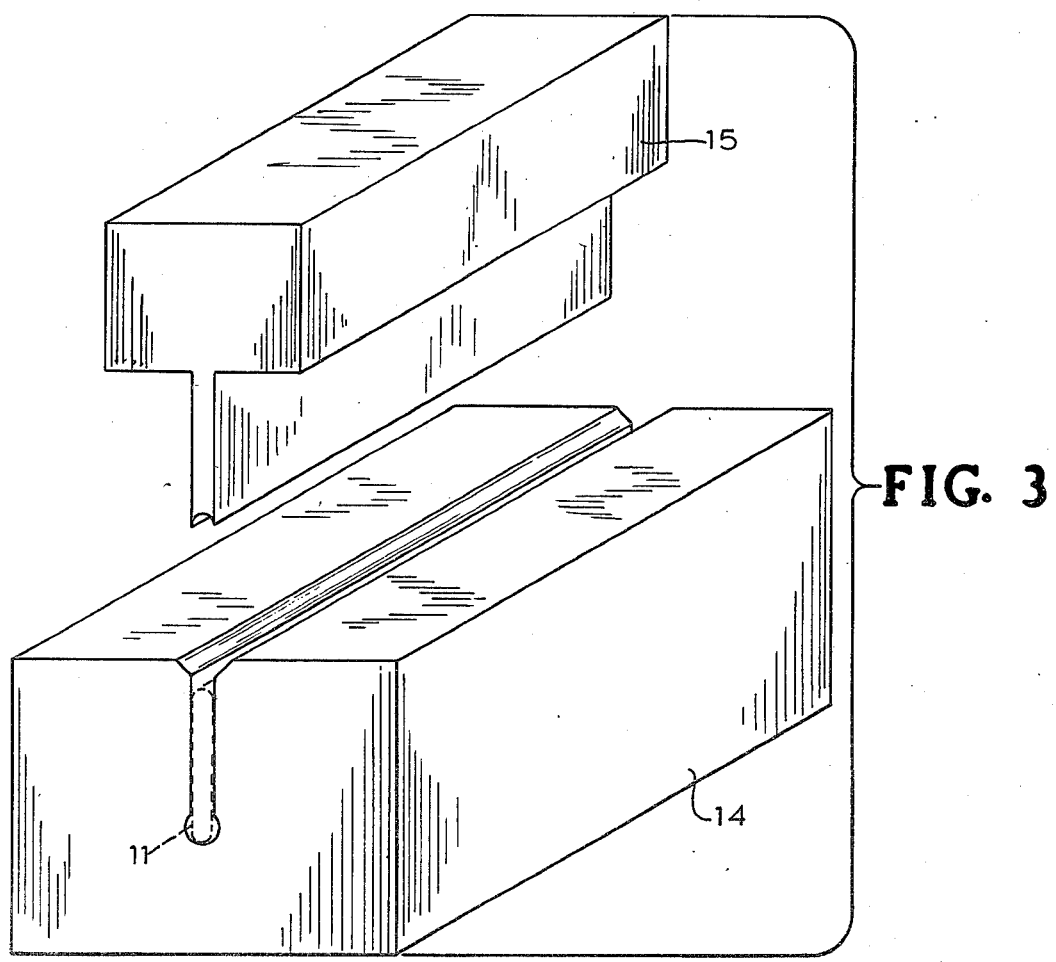
FIG. 3 is a perspective view of a press of the type used to form the dilator of the present invention with the foam material of FIG. 2 illustrated in dashed lines in the base of the press.

Next, the magnesium sulfate impregnated preformed sponge 11 is compressed radially until the density of the resulting cylinder approaches the weighted average density of the sponge material and magnesium sulfate in their solid form. This radial compression and densification of impregnated sponge 11 is preferably done in two steps. First, sponge 11 is compressed into a slab shape, see FIG. 2, and then the slab shaped sponge is placed on edge in a press or die base 14, see FIG. 3, and pressed into a cylinder by inserting die top 15 and pressing the slab shaped sponge as seen in FIG. 3. The resulting cylinder or rod has 1/5 to 1/10 the cross-sectional area of the original cylinder. For example, the diameter A' of the finished product seen in FIG. 4 may be within the range of 3 to 5 mm while the length B' remains within the range of 50 to 80 mm. After any necessary smoothing of the dilator surface, packaging and sterilization, dilators 10 are then ready for clinical use.

Osmotic dilators 10 are introduced into the cervical canal and left in place for up to 24 hours. Dilation of the cervical canal takes place by the displacement of fluid from the surrounding tissue. The magnesium sulfate in dilator 10 is an osmotic substance which draws out and retains the fluid from the cervical tissue, thereby producing gradual dilation of the cervical canal without any trauma.

Osmotic dilator 10 is also made in various sizes for selection based on the size of the internal os of the cervix and on the desired final diameter of dilation. In addition, it may be convenient to use several small dilators 10 at once rather than one large size dilator 10. Thus, the final dilation diameter is a function of the initial diameter of osmotic dilator 10, or on the number of dilators 10 used.

Softening and dilation of the cervix is based on the osmotic removal of water from the tissue and not on the radial forces applied to the cervical ostium as dilator 10 expands. Use of a uterine sound or other conventional dilator of appropriate size may be desirable as a preparatory step for some patients and mechanical forces exerted by the swelling of dilator 10 may be used to enhance the osmotic effect. However, typically the use of such mechanical dilation or forces would not be deemed essential to use of the dilator of the invention. Dilation takes place over a period varying from a few hours to as much as 24 hours depending on the circumstances.

What is claimed is:

1. A cervical dilator adapted for dilating a cervix over a period of hours by withdrawing fluid from the cervix by osmosis without exerting traumatic dilating force on the cervix, comprising a compressed biocompatible foam sponge containing a tissue compatible salt having high osmotic activity sufficient to osmotically displace fluid from the cervix, the sponge being adapted to absorb and retain the displaced fluid without exerting traumatic force on the cervix.

2. The cervical dilator as described in claim 1, wherein the salt is magnesium sulfate.

3. The cervical dilator as described in claim 1, wherein the sponge comprises a polyvinyl alcohol sponge.

4. The cervical dilator as described in claim 1, wherein the sponge comprises a polyurethane sponge.

5. The cervical dilator as described in claim 1, wherein the sponge comprises a silicone sponge.

6. The cervical dilator as described in claim 1, wherein the sponge comprises a collagen sponge.

7. The cervical dilator as described in claim 1, wherein the sponge has a porosity of at least 80% prior to compression and loading with the salt.

8. The cervical dilator as described in claim 7, wherein the salt comprises about 5 wt. % of said sponge.

9. The cervical dilator as described in claim 1, wherein the cross-sectional area of the compressed sponge is about 10% of the cross-sectional area of the sponge before compression.

10. A method of dilating a cervix over a period of hours by withdrawing fluid from the cervix by osmosis without exerting traumatic dilating force on the cervix comprising the steps of:
(a) placing a dilator, comprising a compressed biocompatible foam sponge containing a tissue compatible salt of high osmotic activity sufficient to osmotically displace fluid from the cervix without exerting traumatic force on the cervix, in close proximity to the cervix in order to bring the salt into osmotic communication with the cervix;
(b) gradually releasing the salt in amounts adapted to osmotically displace fluid from the cervical tissue; and
(c) absorbing with the sponge the displaced fluid from the cervical tissue thereby allowing the cervix to soften over said period of hours and dilating the cervix without exerting traumatic dilating forces thereon.

11. The method as described in claim 10, wherein the salt is magnesium sulfate.

12. The method as described in claim 10, wherein the sponge comprises a polyvinyl alcohol sponge.

13. The method as described in claim 10, wherein the sponge comprises a polyurethane sponge.

14. The method as described in claim 10, wherein the sponge comprises a silicone sponge.

15. The method as described in claim 10, wherein the sponge comprises a collagen sponge.

16. A method of making a cervical dilator adapted for dilating a cervix over a period of hours by withdrawing fluid from the cervix by osmosis without exerting traumatic dilating force on the cervix, comprising the steps of:
(a) filling the voids in a biocompatible compressible sponge with a saturated solution of a salt having high osmotic activity sufficient to osmotically displace fluid from the cervix;
(b) removing substantially all of the water from the sponge until the salt containing sponge has approximately 5 wt. % of the salt; and
(c) compressing the sponge until the density of the salt containing sponge approaches the weighted average density of the sponge and the salt and the sponge has a size and shape adaptable for placement in close proximity to the interior of the cervix without exerting traumatic dilating force thereon.

17. The method as described in claim 16, wherein the salt is magnesium sulfate.

18. The method as described in claim 16, wherein the sponge comprises a polyvinyl alcohol sponge.

19. The method as described in claim 16, wherein the sponge comprises a polyurethane sponge.

20. The method as described in claim 16, wherein the sponge comprises a silicone sponge.

21. The method as described in claim 16, wherein the sponge comprises a collagen sponge.